Figures 1, 2:
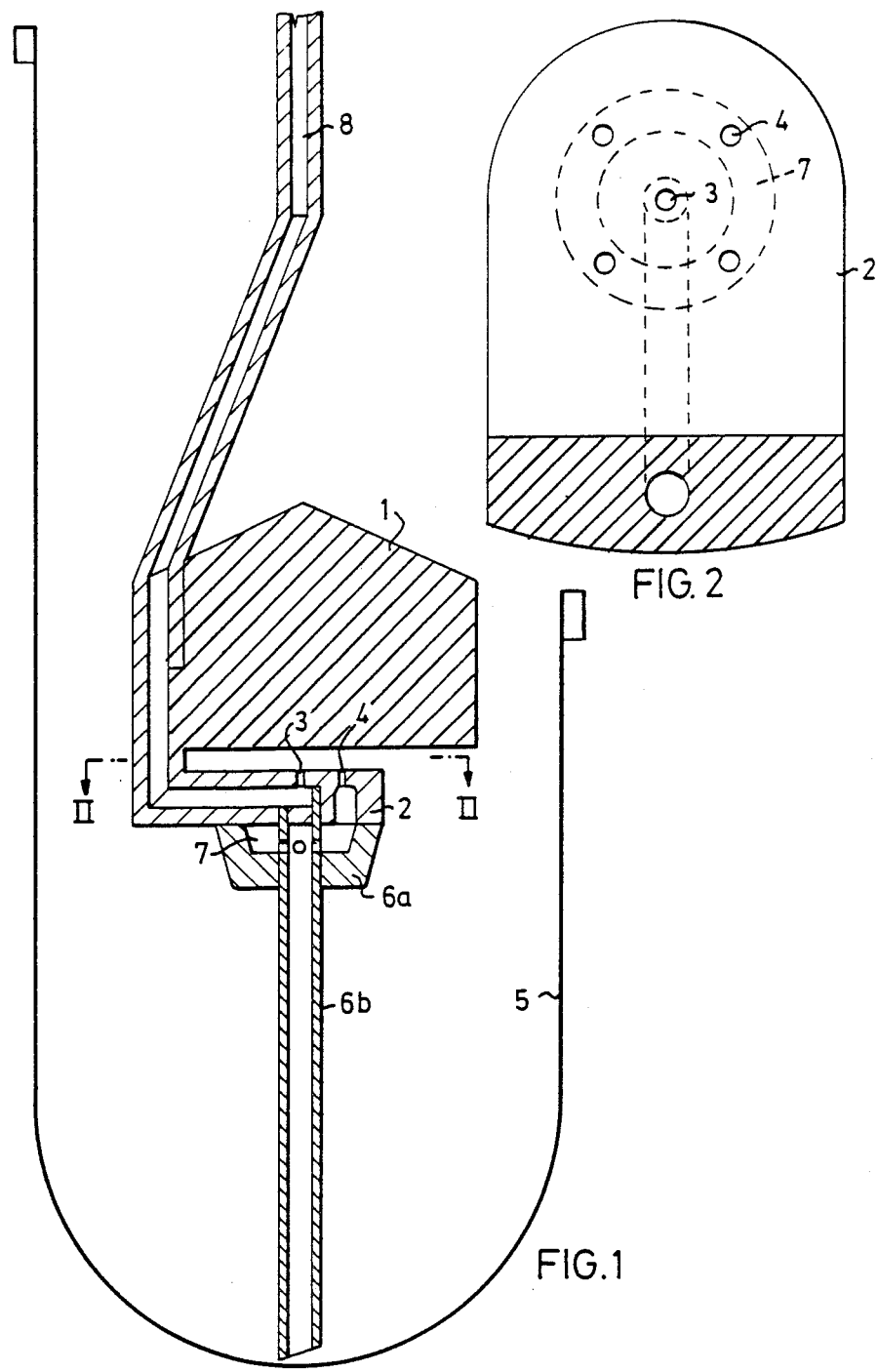

United States Patent [19]

Arborelius, Jr.

[11] Patent Number: 4,757,812
[45] Date of Patent: Jul. 19, 1988

[54] NEBULISER FOR HOMOGENOUS MICRO-AEROSOL

[76] Inventor: Mans Arborelius, Jr., Kastanjeallén 18, S-23044 Vintrie, Sweden

[21] Appl. No.: 11,357

[22] Filed: Jan. 15, 1987

Related U.S. Application Data

[63] Continuation of Ser. No. 770,872, filed as PCT SE84/00427, Dec. 14, 1984, published as WO85/02777, Jul. 4, 1985, abandoned.

[30] Foreign Application Priority Data

Dec. 19, 1983 [SE] Sweden .................. 8307007

[51] Int. Cl.$^4$ .................................. A61M 11/00
[52] U.S. Cl. .................. 128/200.21; 239/338; 239/DIG. 7
[58] Field of Search .............. 128/200.18, 200.21; 239/338, 343, 370, 434, 426, 424.5, DIG. 7

[56] References Cited

U.S. PATENT DOCUMENTS

| | | | |
|---|---|---|---|
| 1,042,556 | 10/1912 | Holland et al. | 128/200.21 |
| 2,840,417 | 6/1958 | Dorsak et al. | 239/338 |
| 2,906,463 | 9/1959 | Curry | 128/200.21 |
| 3,009,826 | 11/1961 | Straughn et al. | 239/434 |
| 3,236,456 | 2/1966 | Ramis | 239/338 |
| 4,231,973 | 11/1980 | Young | 239/338 |
| 4,512,341 | 4/1985 | Lester | 128/200.18 |

Primary Examiner—Edward M. Coven
Assistant Examiner—J. P. Lacyk
Attorney, Agent, or Firm—Brumbaugh, Graves, Donohue & Raymond

[57] ABSTRACT

An apparatus for production of ultra-fine homogenous aerosols, or a nebuliser, is described comprising a Coanda-plate (1) and a liquid channel (3) opening in the vicinity thereof, preferably through an orifice plate (2). The apparatus is useful for producing a micro-aerosol in medical treatment and in other fields. The aerosol is produced from a liquid film formed on the Coanda-plate, which film flows over the plate under radial thinning and breaks into small homogenous droplets at the edge of said plate. Preferably the apparatus is provided with a liquid container (5) surrounding the Coanda-plate.

10 Claims, 1 Drawing Sheet

NEBULISER FOR HOMOGENOUS MICRO-AEROSOL

This application is a continuation of application Ser. No. 770,872, filed as PCT SE84/00427, Dec. 14, 1984, published as WO85/02777, Jul. 4, 1985, now abandoned.

TECHNICAL FIELD

The present invention is related to an apparatus for production of an ultra-fine homogenous aerosol, also referred to as a nebuliser. The invention is also related to production of an ultra-fine homogenous aerosol using such apparatus. The invention is applicable to medical treatment and to other fields where aerosols are used.

BACKGROUND ART

Nebulisers for production of technical or medical aerosols exist in three main types. The oldest, the so-called jet aerosol apparatus consists of an ejection orifice which gives an expanding flow of air which passes tightly above a tube for the liquid which is to be nebulised. By the pressure reduction in the expanding flow of air the liquid is aspirated in the shape of fine drops from the liquid tube and hits a so-called baffle, where the drips are decomposed into an aerosol, normally characterized by particles from below 1 μm to 10–20 μm, that is an inhomogenous aerosol.

Ultrasound nebulisers are ultrasound waves with high power, which tears part the surface layer in a liquid container. They generate an aerosol with even but relatively large particles, often about 4 μm. However the liquid is heated considerably. So-called "spinning disc" nebulisers use a turbine disc which rotates 20.000 rounds/min. or more. Liquid is supplied at the centre of the disc and forms a thin film which is torn apart at the edge of the disc to a fine aerosol wherein the size can be varied but wherein sub-micronic and homogenous particles can be obtained. The apparatus is not suitable for medical use, expensive and not entirely free of danger.

DISCLOSURE OF THE INVENTION

The present invention is related to an apparatus as defined in the appended claims, for production of medical or technical aerosols at a homogenous size, which can be varied depending on the design of the apparatus and obtained in a size suitable for small airways to more than 90%, while conventional jet aerosols are captured in the upper airways. The apparatus can be used to administer pharmaceuticals in fine airways or in general after resorption in the alveols with an efficiency that was previously impossible. It can also be used for production of technical aerosols of a homogenous size with high efficiency and density.

The invention is characterized in that an air jet is generated between a small and a big plate and by the Coanda-effect follows the big plate radially towards the periphery. At the same time a reduced pressure is created between the big plate, here named the Coanda-plate, and the smaller orifice plate. At a suitable distance from the air orifice is a narrow slit or a suitable number of liquid orifices through which the liquid to be nebulised is aspirated. The liquid is carried by the fast expanding air layer towards the periphery of the Coanda-plate where the thin liquid film bursts into fine homogenous particles while nonnebulised liquid hits the wall of the liquid container and runs back to the bottom thereof where an aspiration tube opens and aspirates liquid to the liquid orifice.

The characteristics of the aerosol can be varied between wide limits by varying the forcing pressure in the air flow, the distance between the Coanda-plate and the orifice part, the diameter of the air orifice and liquid orificies and the diameter of the Coanda-plate and the distance between said plate and the wall of the container. The invention is thus not limited to certain embodiments of these details and neither to variations of the surface of the Coanda-plate, that is said plate can also be designed as a spherical or concave surface with varying shape without departing form the main aim of the invention. What is important is that air and/or an energy-rich flow of liquid follows a plate through the so-called Coanda-effect and the final aerosol is formed at the edge thereof by the liquid film being liberated and bursting largely like in a "spinning disc" apparatus. By the fact that the aerosol is generated in a similar manner as in a "spinning disc" apparatus a fine homogenous aerosol is obtained at the same time as the apparatus can be made small and easy to handle. The number of particles generated per unit of volume of air will also be high.

The invention will be described below with a reference to the appended drawings which illustrate an example on a selected and practically tested embodiment.

FIG. 1 is a vertical cross-section of an apparatus according to this invention, and FIG. 2 is a section along the line II—II in FIG. 1.

In the drawing 1 denotes a plate referred to as a Coanda-plate. 2 denotes an orifice plate having at the centre thereof an air orifice 3 to which air is supplied via an air tube 8 connected via an air channel to the air orifice 3. Means for supplying liquid are provided as four liquid orifices 4 in the orifice plate 2. A liquid container is denoted 5. Via a connection part 6a a liquid aspiration tube 6b is connected to a liquid channel 7 forming liquid communication between the bottom of the container 5 and the liquid orifices 4. Compressed air can be supplied to the air orifice via an air tube 8.

According to a useful illustrative example the nebuliser part is made of stainless steel. The Coanda-plate 1 has a diameter of 12 mm and the orifice plate 2 a diameter of 5 mm. The distance between 1 and 2 is 0.8 mm. The air orifice 3 has a diameter of 0.3 mm. The liquid container consists of glass or polished stainless steel cylinder and has the diameter 18 mm and forms a container for the nebulisation liquid and conducts out aerosol formed. Via the aspiration tube 6 liquid is aspirated from the bottom of the container 5 to the liquid orifices 4 via the distribution channel 7. A suitable number of liquid orifices 4 are disposed radially around the air orifice at a distance of 1–2 mm with a diameter of 0.4 mm in this design. The mantle of the distribution channel or connection part 6a and the tube 6b are releasably attached to the orifice plate 2 with tin soldering to enable cleaning of the channels 3 and 4. With a pressure of air or oxygen at about 600 kPa the apparatus produces 4.5 liters of aerosol/min with a liquid content of 0.13–0.15 ml. The particle size after drying is 0.3 μm (mean mass diameter) and the particle density $3 \times 10^8 \times cm^{-3}$ as compared to not more than $2.8 \times 10^7 \times cm^{-3}$ for the best aerosol apparatus now used in medical practice.

A similar performance can be obtained if the distance between the orifice part and the Coanda-plate is decreased to 0.1 mm and the diameter of the orifice 3 to 0.2 mm and on the plate 2 to 2 mm. The previous liquid aspiration system is eliminated, and the nebulisation liquid is introduced via the previous air channel and the orifice with a pressure of about 10 kPa for example from a pump of the kind that is used in alternating current powered airless spray painting pistols. The aspiration conduit to the pump is in such cases connected to a tube which opens at the bottom of the container. This embodiment is believed to be superior if one wishes to make an electric powered variant of the nebuliser and will be considerably less expensive than the alternative with an electric-powered aircompressor.

If a small portable variant of the air-powered nebuliser is desired a compressed air bottle of about 0.5 litre with a pressure of 30.000 kPa is recommended, which gives the apparatus a capacity of at least 6 occasions of treatment of 5 minutes each, that is a capacity of up to 2 days of treatment at the diseases that are in consideration.

The apparatus enables supply of drugs to distal airways to more than 90% while aerosols from conventional apparatus are deposed in the oral cavity or throat to about 85%. The apparatus thus enables therapy with local $\beta_2$-agonists or steroids with an efficiency that was previously impossible to achieve, but should in other embodiments be useful for producing technical aerosols for different purposes.

In combination with an evaporation tube it gives the possibility of studying the distribution of ventilation in the lungs with $^{99}$Tc without disturbing activity in the upper airways or throat, and with a yield in the lungs 5–10 times greater than with apparatus now in use.

I claim:

1. An apparatus for producing an ultrafine aerosol comprising
   A. a Coanda plate upon which said aerosol is first formed;
   B. a small orifice plate which is parallel to and at a distance from said Coanda plate, thereby forming a channel between said plates,
      (1) said Coanda plate having a periphery extending beyond said orifice plate through at least a portion of the periphery thereof,
      (2) said orifice plate having therethrough a central fluid orifice opposite a substantially central point in the Coanda plate for discharge of a fluid into said channel, and means for supplying fluid thereto, the velocity of fluid exiting said channel and the distance between said Coanda plate and orifice plate being so related to each other and to the fluid exiting said channel as to first form the ultrafine aerosol on the Coanda plate by means of a Coanda effect in which a film of flowing fluid adhering to said Coanda plate passes over the portion of said Coanda plate which extends beyond said orifice plate,
      (3) and at least one liquid supply orifice through said orifice plate for discharge of liquid into said channel, which liquid is picked up by said fluid and becomes a part of the fluid stream passing over the portion of said Coanda plate which extends beyond said orifice plate;
   C. whereby the Coanda effect thereby generated causes said flow of flowing fluid containing said liquid to expend progressively to the periphery of said Coanda plate, which Coanda effect causes the liquid carried by said fluid to first break into an ultrafine aerosol as it leaves the periphery of said Coanda plate.

2. An apparatus for producing an ultrafine aerosol according to claim 1 wherein the means for supplying fluid to the fluid orifice includes a source of compressed air and an air tube connected at one end to the source of compressed air, which air tube at an opposite end is in communication with said fluid orifice.

3. An apparatus for producing an ultrafine aerosol according to claim 1 further comprising (A) a liquid container for collection at the bottom thereof of liquid not formed into an aerosol on said Coanda plate by said Coanda effect; (B) a liquid channel in communication with said liquid supply orifice; and (C) a liquid aspiration tube inserted at one end into the bottom of said liquid container and connected at an opposite end to said liquid channel; (D) whereby a liquid communication is formed between the bottom of said liquid container and said liquid orifice such that liquid collected in the bottom of said liquid container is aspirated through said aspiration tube and flows through said liquid supply orifice to said Coanda plate on which said liquid is first formed into an aerosol.

4. An apparatus for producing an ultrafine aerosol according to claim 1 wherein a plurality of said liquid supply orifices are radially disposed about said central fluid orifice in said orifice plate.

5. An apparatus for producing an ultrafine aerosol according to claim 1 wherein the distance between said Coanda plate and said orifice plate is between 0.1 and 0.8 mm.

6. An apparatus for producing an ultrafine aerosol according to claim 1 wherein the distance between said Coanda plate and said orifice plate is 0.8 mm.

7. An apparatus for producing an ultrafine aerosol according to claim 1 wherein the distance between said Coanda plate and said orifice plate is 0.1 mm.

8. A method for producing an ultrafine aerosol by a Coanda effect comprising
   A. discharging a fluid into a channel between a Coanda plate on which the ultrafine aerosol is first formed, and an orifice plate, which is parallel to and at a distance from said Coanda plate;
      (1) said Coanda plate having a periphery extending beyond said orifice plate through at least a portion of the periphery thereof,
      (2) said orifice plate having therethrough a central fluid orifice opposite a substantially central point in said Coanda plate through which said fluid is discharged and at least one liquid supply orifice radially disposed around said central fluid orifice;
   B. the velocity of fluid existing said channel, and the size of the channel between said Coanda plate and said orifice plate being so related to each other and the fluid discharged as to generate a Coanda effect wherein a film of flowing fluid adhering to said Coanda plate passes over a portion of said Coanda plate beyond said orifice plate;
   C. supplying a liquid through said liquid supply orifice into said channel, which liquid is picked up by said fluid film and becomes a part thereof passing over the portion of said Coanda plate extending beyond said orifice plate;
   D. whereby the Coanda effect thus generated causes said flow of flowing fluid containing said liquid to expand progressively to the periphery of said Coanda plate, which Coanda effect causes the liquid carried by said fluid to first break into an ultrafine aerosol as it leaves the periphery of said Coanda plate.

9. A method for producing an ultrafine aerosol by a Coanda effect according to claim 8 wherein the aerosol is used for medical treatment.

10. A method for producing an ultrafine aerosol by a Coanda effect according to claim 9 wherein the aerosol is used for inhalation.

* * * * *